(12) United States Patent
Lee et al.

(10) Patent No.: US 10,598,510 B2
(45) Date of Patent: Mar. 24, 2020

(54) STEP COUNTER DEVICES AND STEP COUNTING METHODS

(71) Applicant: RAZER (ASIA-PACIFIC) PTE. LTD., Singapore (SG)

(72) Inventors: Kah Yong Lee, Singapore (SG); Qiang Wang, Singapore (SG); Xiaohui Liu, Singapore (SG)

(73) Assignee: RAZER (ASIA-PACIFIC) PTE. LTD., Singapore (SG)

(*) Notice: Subject to any disclaimer, the term of this patent is extended or adjusted under 35 U.S.C. 154(b) by 335 days.

(21) Appl. No.: 15/529,149

(22) PCT Filed: Nov. 27, 2014

(86) PCT No.: PCT/SG2014/000558
§ 371 (c)(1),
(2) Date: May 24, 2017

(87) PCT Pub. No.: WO2016/085403
PCT Pub. Date: Jun. 2, 2016

(65) Prior Publication Data
US 2017/0343378 A1    Nov. 30, 2017

(51) Int. Cl.
*G01C 22/00*    (2006.01)
*G01C 21/16*    (2006.01)
(Continued)

(52) U.S. Cl.
CPC ........... *G01C 22/006* (2013.01); *A61B 5/112* (2013.01); *A61B 5/1112* (2013.01); *G01C 21/16* (2013.01); *A63B 24/0062* (2013.01); *G16H 40/63* (2018.01)

(58) Field of Classification Search
CPC ..... G01C 22/006; G01C 21/16; A61B 5/1112; A61B 5/112; G16H 40/63; A63B 24/006
See application file for complete search history.

(56) References Cited

U.S. PATENT DOCUMENTS

| 6,513,381 B2 | 2/2003 | Fyfe et al. |
| 7,334,472 B2 | 2/2008 | Seo et al. |

(Continued)

FOREIGN PATENT DOCUMENTS

| CN | 1670483 A | 9/2005 |
| CN | 103616034 A | 3/2014 |

(Continued)

OTHER PUBLICATIONS

Extended European Search Report dated Jun. 27, 2018, 7 pages, for the corresponding European Patent Application No. 14906949.4.
(Continued)

*Primary Examiner* — Mohammad K Islam
(74) *Attorney, Agent, or Firm* — Polsinelli PC

(57) ABSTRACT

According to various embodiments, a step counter device may be provided. The step counter device may include an accelerometer configured to determine an acceleration in each axis of a plurality of axes; a dominant axis determination circuit configured to determine one axis of the plurality of axis as a dominant axis based on determining, for each axis of the plurality of axis, a first plurality of criteria for the respective axis; and a step number determination circuit configured to determine a number of steps based on determining a second plurality of criteria for the dominant axis.

18 Claims, 3 Drawing Sheets

(51) Int. Cl.
*G06F 19/00* (2018.01)
*A61B 5/11* (2006.01)
*A63B 24/00* (2006.01)
*G16H 40/63* (2018.01)

(56) References Cited

U.S. PATENT DOCUMENTS

| | | | |
|---|---|---|---|
| 7,457,719 B1 | 11/2008 | Kahn et al. | |
| 7,596,467 B2 | 9/2009 | Sugai | |
| 7,647,196 B2 | 1/2010 | Kahn et al. | |
| 7,653,508 B1* | 1/2010 | Kahn | G01B 21/02 33/700 |
| 7,698,097 B2 | 4/2010 | Pasolini et al. | |
| 7,725,289 B2 | 5/2010 | Nagashima et al. | |
| 7,753,861 B1* | 7/2010 | Kahn | A61B 5/1118 482/8 |
| 8,042,390 B2 | 10/2011 | Pasolini et al. | |
| 8,311,768 B2 | 11/2012 | Fukutome et al. | |
| 8,712,723 B1 | 4/2014 | Kahn et al. | |
| 9,128,116 B2* | 9/2015 | Welch | G01P 21/00 |
| 9,628,958 B1* | 4/2017 | McBurney | H04W 4/027 |
| 9,983,224 B2* | 5/2018 | Pakzad | G01P 15/00 |
| 2006/0112754 A1 | 6/2006 | Yamamoto et al. | |
| 2006/0220882 A1 | 10/2006 | Makino | |
| 2009/0234614 A1* | 9/2009 | Kahn | G02C 5/001 702/141 |
| 2009/0240461 A1* | 9/2009 | Makino | A61B 5/1123 702/141 |
| 2009/0319221 A1* | 12/2009 | Kahn | A61B 5/1123 702/141 |
| 2010/0024531 A1* | 2/2010 | Senoo | A63B 24/0021 73/65.01 |
| 2010/0056872 A1* | 3/2010 | Kahn | A61B 5/1038 600/300 |
| 2011/0172909 A1* | 7/2011 | Kahn | G01C 21/165 701/533 |
| 2012/0041713 A1* | 2/2012 | Bonnet | A61B 5/1038 702/160 |
| 2012/0136573 A1* | 5/2012 | Janardhanan | G01C 21/165 701/512 |
| 2013/0085700 A1* | 4/2013 | Modi | G01C 22/006 702/104 |
| 2013/0110011 A1 | 5/2013 | McGregor et al. | |
| 2013/0191069 A1* | 7/2013 | Ravindran | G01C 22/006 702/160 |
| 2014/0074431 A1 | 3/2014 | Modi | |
| 2014/0180621 A1* | 6/2014 | Poduri | G01P 21/00 702/96 |
| 2015/0177845 A1* | 6/2015 | Szacherski | G06F 3/017 345/156 |
| 2015/0316578 A1* | 11/2015 | Pakzad | G01P 15/00 702/150 |
| 2017/0003140 A1* | 1/2017 | Villien | G01C 21/14 |
| 2017/0188897 A1* | 7/2017 | Thein | A61B 5/7221 |
| 2018/0338708 A1* | 11/2018 | Chan | A61B 5/1118 |

FOREIGN PATENT DOCUMENTS

| | | |
|---|---|---|
| CN | 103997572 A | 8/2014 |
| CN | 104075730 A | 10/2014 |
| EP | 1813916 A1 | 8/2007 |
| KR | 10-2008-0029209 A | 4/2008 |
| WO | 2008/133921 A1 | 11/2008 |
| WO | 2013/169755 A2 | 11/2013 |

OTHER PUBLICATIONS

Office Action dated Jan. 19, 2020, in 5 pages, for the corresponding Chinese Patent Application No. 201480084565.0.

* cited by examiner

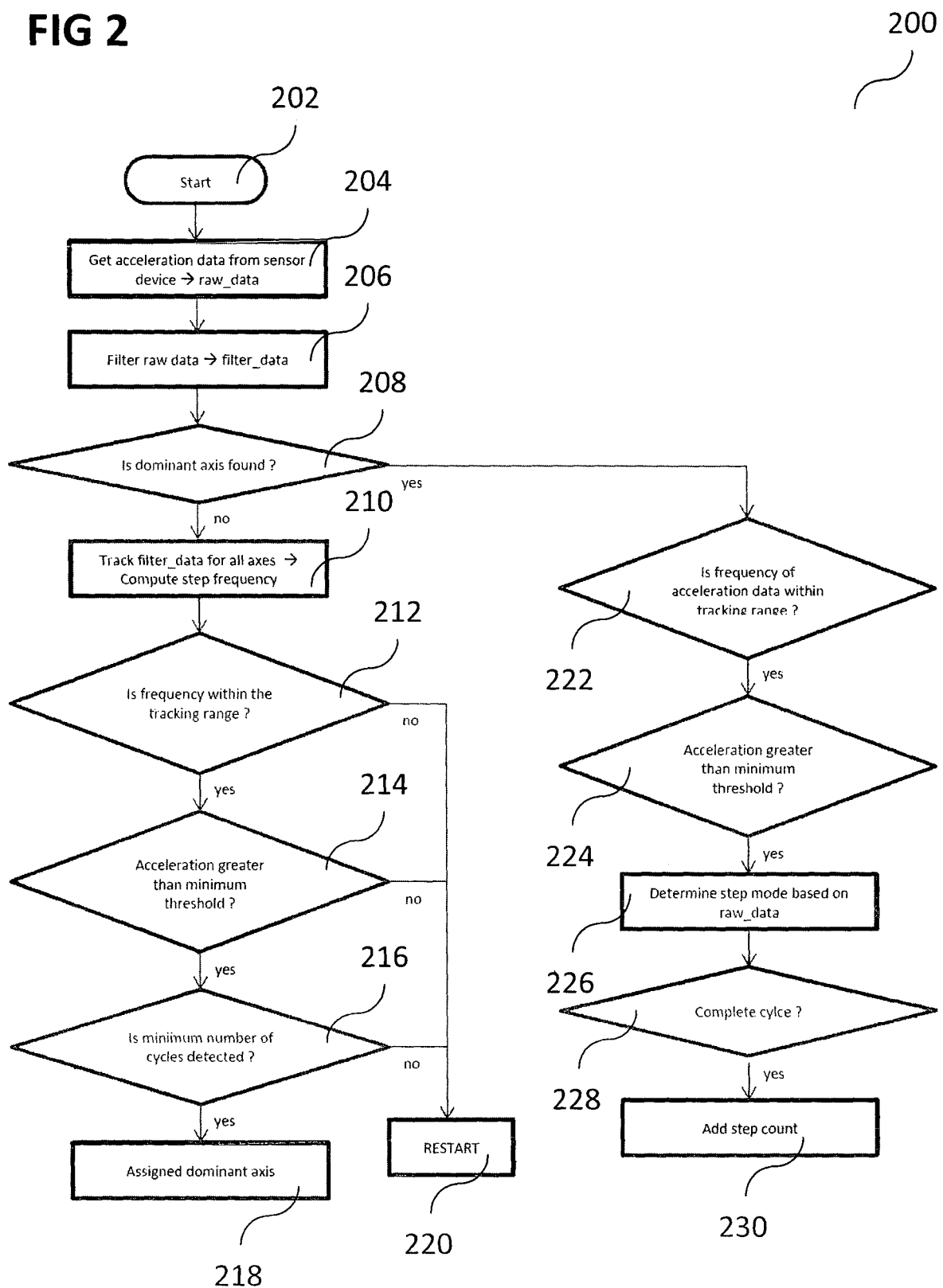

STEP COUNTER DEVICES AND STEP COUNTING METHODS

TECHNICAL FIELD

Various embodiments generally relate to step counter devices and step counting methods.

BACKGROUND

The number of steps a person takes during a pre-determined period, for example during a day or during a training session, may be a valuable indicator, for example for assessing further training goals. As such, there may be a need for an efficient way to determine the number of steps taken by a person.

SUMMARY OF THE INVENTION

According to various embodiments, a step counter device may be provided. The step counter device may include an accelerometer configured to determine an acceleration in each axis of a plurality of axes; a dominant axis determination circuit configured to determine one axis of the plurality of axis as a dominant axis based on determining, for each axis of the plurality of axis, a plurality of criteria for the respective axis; a step number determination circuit configured to determine a number of steps based on determining the plurality of criteria for the dominant axis; wherein the criteria for a respective axis may include a criterion indicating whether a frequency of acceleration in the respective axis is within a first pre-determined range, a criterion indicating whether a variation in the frequency of acceleration in the respective axis between various cycles is within a second pre-determined range; a criterion indicating whether a variation in the amplitude of acceleration in the respective axis between various cycles is within a third pre-determined range; and a criterion indicating whether the acceleration in the respective axis is higher than a pre-determined threshold.

According to various embodiments, the threshold (in other words: a minimum acceleration threshold) may be 0.01 g, or may be 0.1 g, or may be 0.5 g, wherein g is a unit of acceleration equal to the acceleration of gravity at the earth's surface (for example about 9.81 m/s$^2$).

According to various embodiments, a step counting method may be provided. The step counting method may include: determining an acceleration in each axis of a plurality of axes; determining one axis of the plurality of axis as a dominant axis based on determining, for each axis of the plurality of axis, a plurality of criteria for the respective axis; determining a number of steps based on determining the plurality of criteria for the dominant axis; wherein the criteria for a respective axis may include a criterion indicating whether a frequency of acceleration in the respective axis is within a first pre-determined range, a criterion indicating whether a variation in the frequency of acceleration in the respective axis between various cycles is within a second pre-determined range; a criterion indicating whether a variation in the amplitude of acceleration in the respective axis between various cycles is within a third pre-determined range; and a criterion indicating whether the acceleration in the respective axis is higher than a pre-determined threshold.

BRIEF DESCRIPTION OF THE DRAWINGS

In the drawings, like reference characters generally refer to the same parts throughout the different views. The drawings are not necessarily to scale, emphasis instead generally, being placed upon illustrating the principles of the invention. The dimensions of the various features or elements may be arbitrarily expanded or reduced for clarity. In the following description, various embodiments of the invention are described with reference to the following drawings, in which:

FIG. 2 shows a flow diagram illustrating a step counting method according to various embodiments.

DETAILED DESCRIPTION

Figure 1A:
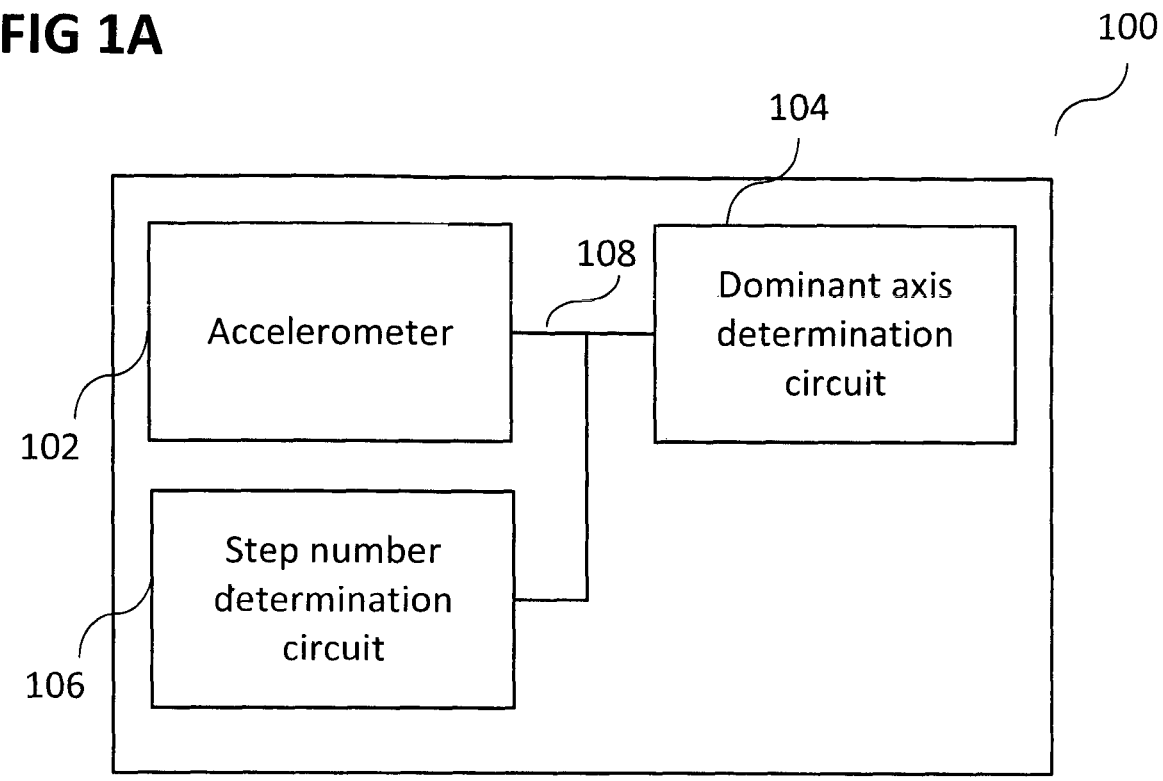
FIG. 1A shows a step counter device according to various embodiments.

The following detailed description refers to the accompanying drawings that show, by way of illustration, specific details and embodiments in which the invention may be practiced. These embodiments are described in sufficient detail to enable those skilled in the art to practice the invention. Other embodiments may be utilized and structural, and logical changes may be made without departing from the scope of the invention. The various embodiments are not necessarily mutually exclusive, as some embodiments can be combined with one or more other embodiments to form new embodiments.

In this context, the step counter device as described in this description may include a memory which is for example used in the processing carried out in the step counter device. A memory used in the embodiments may be a volatile memory, for example a DRAM (Dynamic Random Access Memory) or a non-volatile memory, for example a PROM (Programmable Read Only Memory), an EPROM (Erasable PROM), EEPROM (Electrically Erasable PROM), or a flash memory, e.g., a floating gate memory, a charge trapping memory, an MRAM (Magnetoresistive Random Access Memory) or a PCRAM (Phase Change Random Access Memory).

In an embodiment, a "circuit" may be understood as any kind of a logic implementing entity, which may be special purpose circuitry or a processor executing software stored in a memory, firmware, or any combination thereof. Thus, in an embodiment, a "circuit" may be a hard-wired logic circuit or a programmable logic circuit such as a programmable processor, e.g. a microprocessor (e.g. a Complex Instruction Set Computer (CISC) processor or a Reduced Instruction Set Computer (RISC) processor). A "circuit" may also be a processor executing software, e.g. any kind of computer program, e.g. a computer program using a virtual machine code such as e.g. Java. Any other kind of implementation of the respective functions which will be described in more detail below may also be understood as a "circuit" in accordance with an alternative embodiment.

In the specification the term "comprising" shall be understood to have a broad meaning similar to the term "including" and will be understood to imply the inclusion of a stated integer or step or group of integers or steps but not the exclusion of any other integer or step or group of integers or steps. This definition also applies to variations on the term "comprising" such as "comprise" and "comprises".

The reference to any prior art in this specification is not, and should not be taken as an acknowledgement or any form of suggestion that the referenced prior art forms part of the common general knowledge in Australia (or any other country).

In order that the invention may be readily understood and put into practical effect, particular embodiments will now be described by Way of examples and not limitations, and with reference to the figures.

Various embodiments are provided for devices, and various embodiments are provided for methods. It will be understood that basic properties of the devices also hold for the methods and vice versa. Therefore, for sake of brevity, duplicate description of such properties may be omitted.

It will be understood that any property described herein for a specific device may also hold for any device described herein. It will be understood that any property described herein for a specific method may also hold for any method described herein. Furthermore, it will be understood that for any device or method described herein, not necessarily all the components or steps described must be enclosed in the device or method, but only some (but not all) components or steps may be enclosed.

The term "coupled" (or "connected") herein may be understood as electrically coupled or as mechanically coupled, for example attached or fixed or attached, or just in contact without any fixation, and it will be understood that both direct coupling or indirect coupling (in other words: coupling without direct contact) may be provided.

The number of steps a person takes during a pre-determined period, for example during a day or during a training session, may be a valuable indicator, for example for assessing further training goals. According to various embodiments, an efficient way to determine the number of steps taken by a person may be provided.

According to various embodiments, method and devices (in other words: apparatuses) for measuring step count (in other words: a number of steps) may be provided.

According to various embodiments, step may be counted from (in other words: using) a wearable device (for example a wearable band; for example a wearable wristband; for example a wrist watch). The accuracy of step counting may be greatly affected by the movement of a hand of the user, for example the hand of the user on which the wearable device is mounted. According to various embodiments, the accuracy of the detection may be improved, and a reduced amount of resources (for example using minimal CPU (central processing unit) resources of a CPU provided in the wearable device) may be used.

Users may be more willing to use the (wearable) device on a daily basis if the device is able to detect human activities accurately. According to various embodiments, a product (for example (wearable) device) may be provided which combines sophisticated functions with accurate human activity detection functions.

FIG. 1A shows a step counter device 100 according to various embodiments. The step counter device 100 may include an accelerometer 102 configured to determine an acceleration in each axis of a plurality of axes (for example two axes; for example three axes; for example linear accelerations; for example rotational accelerations; for example at least one linear acceleration and at least one rotational acceleration). The step counter device 100 may further include a dominant axis determination circuit 104 configured to determine one axis of the plurality of axis as a dominant axis based on determining, for each axis of the plurality of axis, a plurality of criteria for the respective axis. The step counter device 100 may further include a step number determination circuit 106 configured to determine a number of steps based on determining the plurality of criteria for the dominant axis (for example only for the dominant axis but not for the other axis or axes different from the dominant axis). The criteria for a respective axis may include (or may be) a criterion indicating whether a frequency of acceleration in the respective axis is within a first pre-determined range, a criterion indicating whether a variation in the frequency of acceleration in the respective axis between various cycles is within a second pre-determined range; a criterion indicating whether a variation in the amplitude of acceleration in the respective axis between various cycles is within a third pre-determined range; and a criterion indicating whether the acceleration in the respective axis is higher than a pre-determined threshold. The accelerometer 102, the dominant axis determination circuit 104, and the step number determination circuit 106 may be may be coupled with each other, like indicated by line 108, for example electrically coupled, for example using a line or a cable, and/or mechanically coupled.

In other words, according to various embodiments a step counter device may be provided which determines a dominant axis based on determining a plurality of criteria for all axis, and then, once the dominant axis is determined, determines a number of steps (for example steps taken by a user of the step counter device) based on determining the plurality of criteria only for the determined dominant axis.

Figure 1C:
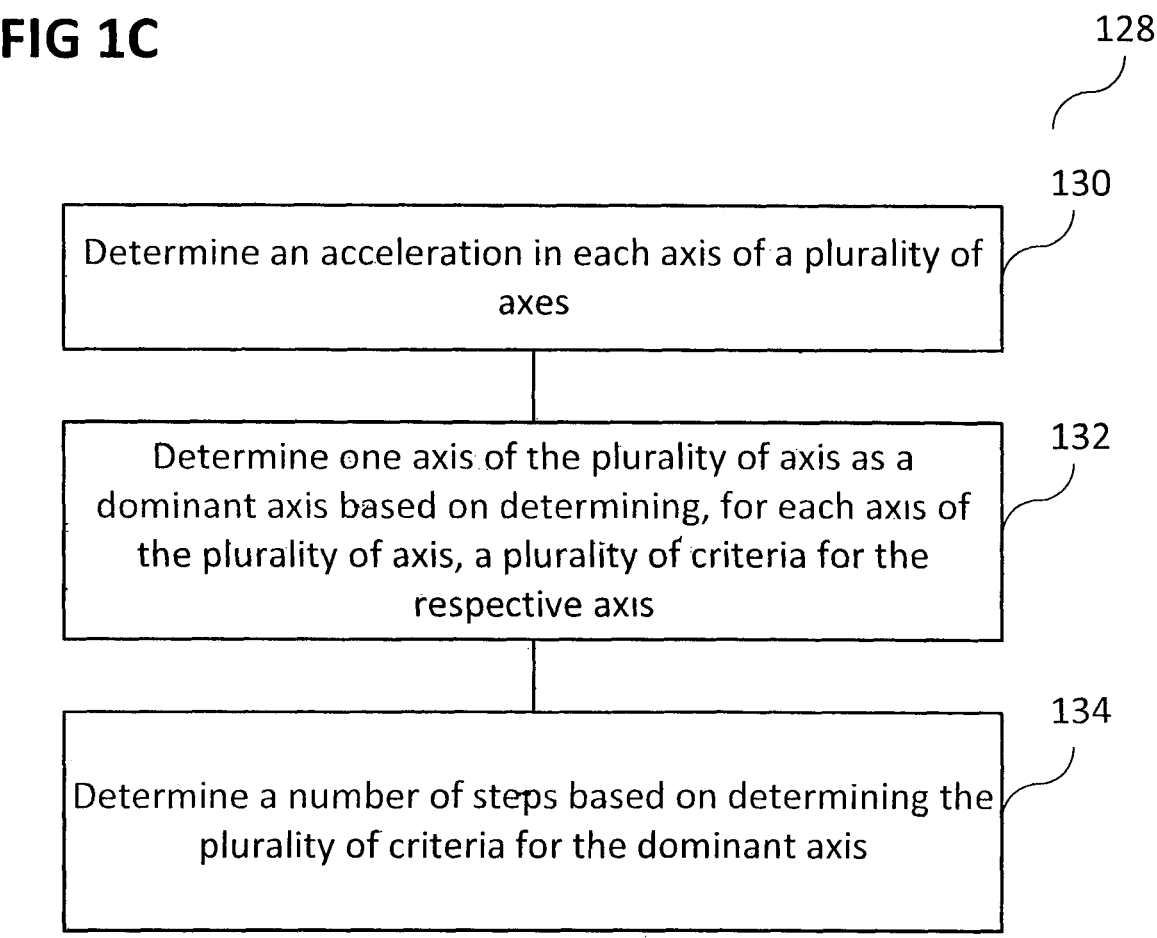
FIG. 1C shows a flow diagram illustrating a step counting method according to various embodiments.
Figure 1B:
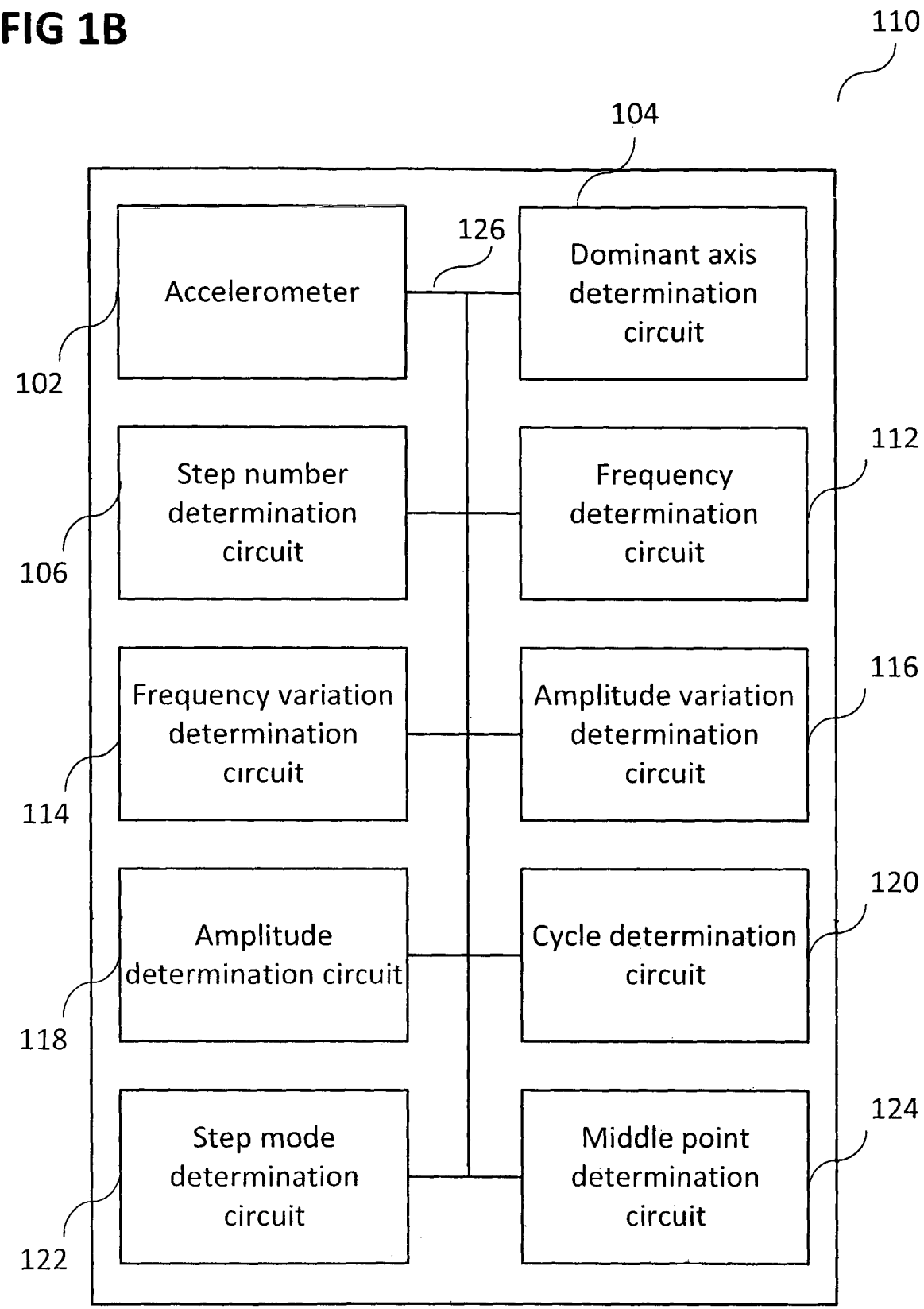
FIG. 1B shows a step counter device according to various embodiments.

FIG. 1B shows a step counter device 110 according to various embodiments. The step counter device 110 may include various portions which may be similar or identical to portions of the step counter device 100 of FIG. 1A, so that the same reference signs may be used and duplicate description may be omitted. The step counter device 110 may, similar to the step counter device 100 of FIG. 1A, include an accelerometer 102 configured to determine an acceleration in each axis of a plurality of axes (for example two axes; for example three axes; for example linear accelerations; for example rotational accelerations; for example at least one linear acceleration and at least one rotational acceleration). The step counter device 110 may, similar to the step counter device 100 of FIG. 1A, further include a dominant axis determination circuit 104 configured to determine one axis of the plurality of axis as a dominant axis based on determining, for each axis of the plurality of axis, a plurality of criteria for the respective axis. The step counter device 110 may, similar to the step counter device 100 of FIG. 1A, further include a step number determination circuit 106 configured to determine a number of steps based on determining the plurality of criteria for the dominant axis (for example only for the dominant axis but not for the other axis or axes different from the dominant axis). The criteria for a respective axis may include (or may be) a criterion indicating whether a frequency of acceleration in the respective axis is within a first pre-determined range, a criterion indicating whether a variation in the frequency of acceleration in the respective axis between various cycles is within a second pre-determined range; a criterion indicating whether a variation in the amplitude of acceleration in the respective axis between various cycles is within a third pre-determined range; and a criterion indicating whether the acceleration in the respective axis is higher than a pre-determined threshold. The step counter device 110 may further include a frequency determination circuit 112, like will be described in more detail below. The step counter device 110 may further include a frequency variation determination circuit 114, like will be described in more detail below. The step counter device 110 may further include an amplitude variation determination circuit 116, like will be described in more detail below. The step counter device 110 may further include an amplitude determination circuit 118, like will be described in more detail below. The step counter device 110 may further include a cycle determination circuit 120, like will be described in more detail below. The step counter device 110 may further include a step mode determination circuit 122, like will be described in more detail below. The step counter device 110 may further include a middle point determination circuit 124, like will be described in more detail below. The accelerometer 102, the dominant axis determination circuit 104, the step number determination circuit 106, the frequency determination circuit 112, the frequency variation determination circuit 114, the amplitude variation determination circuit 116, the amplitude determination circuit 118, the cycle determination circuit 120, the step mode determination circuit 122, and the middle point determination circuit 124 may be may be coupled with each other, like indicated by line 126, for example electrically coupled, for example using a line or a cable, and/or mechanically coupled.

According to various embodiments, the frequency determination circuit 112 may be configured to determine for a respective axis of the plurality of axis the criterion indicating whether the frequency of acceleration in the respective axis is within a pre-determined range.

According to various embodiments, the frequency variation determination circuit 114 may be configured to determine for a respective axis of the plurality of axis the criterion indicating whether the variation in the frequency of acceleration in the respective axis between various cycles is within a pre-determined range.

According to various embodiments, the amplitude variation determination circuit 116 may be configured to determine for a respective axis of the plurality of axis the criterion indicating whether the variation in the amplitude of acceleration in the respective axis between various cycles is within a pre-determined range.

According to various embodiments, the amplitude determination circuit 118 may be configured to determine for a respective axis of the plurality of axis the criterion indicating whether the acceleration in the respective axis is higher than a pre-determined threshold.

According to various embodiments, the first pre-determined range may include or may be at least one of: a range of 0.2 Hz to 20 Hz; a range of 0.5 Hz to 5 Hz; and a range of 1 Hz to 4 Hz.

According to various embodiments, the second pre-determined range may include or may be at least one of: a range of 20% to 80%; a range of 40% to 60%; a value of at least substantially 40%; a value of at least substantially 50%; and a value of at least substantially 60%.

According to various embodiments, the third pre-determined range may include or may be at least one of: a range of 20% to 80%; a range of 40% to 60%; a value of at least substantially 40%; a value of at least substantially 50%; and a value of at least substantially 60%.

According to various embodiments, the pre-determined threshold may include or may be 0.01 g, or may be 0.1 g, or may be 0.5 g, wherein g is a unit of acceleration equal to the acceleration of gravity at the earth's surface (for example about 9.81 m/s$^2$).

According to various embodiments, the dominant axis determination circuit 104 may further be configured to determine the dominant axis based on determining, for each axis of the plurality of axes, a criterion indicating whether the acceleration in the respective axis includes at least a pre-determined number of cycles.

According to various embodiments, the cycle determination circuit 120 may be configured to determine a cycle of acceleration in any one of the plurality of axes.

According to various embodiments, the step mode determination circuit 122 may be configured to determine a step mode based on the accelerations determined by the accelerometer.

According to various embodiments, the middle point determination circuit 124 may be configured to determine a middle point in the accelerations determined by the accelerometer.

According to various embodiments, the step mode determination circuit 122 may be configured to determine a step mode based on the determined middle point.

According to various embodiments, the step counter device 110 may be provided in or may be or may include or may be included in a wearable device.

FIG. 1C shows a flow diagram 128 illustrating a step counting method according to various embodiments. In 130, an acceleration may be determined in each axis of a plurality of axes. In 132, one axis of the plurality of axis may be determined (in other words: may be selected) as a dominant axis based on determining, for each axis of the plurality of axis, a plurality of criteria for the respective axis. In 134, a number of steps may be determined (in other words: may be tracked; in other words: may be counted) based on determining the plurality of criteria for the dominant axis. The criteria for a respective axis may include or may be a criterion indicating whether a frequency of acceleration in the respective axis is within a first pre-determined range, a criterion indicating whether a variation in the frequency of acceleration in the respective axis between various cycles is within a second pre-determined range; a criterion indicating whether a variation in the amplitude of acceleration in the respective axis between various cycles is within a third pre-determined range; and a criterion indicating whether the acceleration in the respective axis is higher than a pre-determined threshold.

According to various embodiments, the step counting method may further include determining for a respective axis of the plurality of axis the criterion indicating whether the frequency of acceleration in the respective axis is within a pre-determined range.

According to various embodiments, the step counting method may further include determining for a respective axis of the plurality of axis the criterion indicating whether the variation in the frequency of acceleration in the respective axis between various cycles is within a pre-determined range.

According to various embodiments, the step counting method may further include determining for a respective axis of the plurality of axis the criterion indicating whether the variation in the amplitude of acceleration in the respective axis between various cycles is within a pre-determined range.

According to various embodiments, the step counting method may further include determining for a respective axis of the plurality of axis the criterion indicating whether the acceleration in the respective axis is higher than a pre-determined threshold.

According to various embodiments, wherein the first pre-determined range may include or may be at least one of: a range of 0.2 Hz to 20 Hz; a range of 0.5 Hz to 5 Hz; and a range of 1 Hz to 4 Hz.

According to various embodiments, the second pre-determined range may include or may be at least one of: a range of 20% to 80%; a range of 40% to 60%; a value of at least substantially 40%; a value of at least substantially 50%; and a value of at least substantially 60%.

According to various embodiments, the third pre-determined range may include or may be at least one of: a range of 20% to 80%; a range of 40% to 60%; a value of at least substantially 40%; a value of at least substantially 50%; and a value of at least substantially 60%.

According to various embodiments, the pre-determined threshold may include or may be 0.01 g, or may be 0.1 g, or may be 0.5 g, wherein g is a unit of acceleration equal to the acceleration of gravity at the earth's surface (for example about 9.81 m/s$^2$).

According to various embodiments, the step counting method may further include determining the dominant axis based on determining, for each axis of the plurality of axes, a criterion indicating whether the acceleration in the respective axis includes at least a pre-determined number of cycles.

According to various embodiments, the step counting method may further include determining a cycle of acceleration in any one of the plurality of axes.

According to various embodiments, the step counting method may further include determining a step mode based on the determined accelerations.

According to various embodiments, the step counting method may further include determining a middle point in the determined accelerations.

According to various embodiments, the step counting method may further include determining a step mode based on the determined middle point.

According to various embodiments, the step counting method may be performed (in other words: carried out; in other words: performed) in a wearable device.

According to various embodiments, devices and methods may be provided for determining the number of steps taken by measuring a proper acceleration experienced by an acceleration sensor device: The sensor device may be part of a wearable device, which may be fitted to a human body.

FIG. 2 shows a flow diagram 200 illustrating a method for determining a step count according to various embodiments. The method may start in 202. Acceleration data may be acquired from a sensor device in 204; the acquired data may be referred to as raw data.

In 206, the raw data may be filtered (and as such, filtered data may be acquired). For example, all raw acceleration data may be processed by a low pass filter to filter the high frequency noise and an averaging filter to remove the DC (direct current; in other words: constant or not changing) component. The resultant data may be named (or called) filtered data.

According to various embodiments, the measurement of step count (in other words: counting the number of steps) may be divided into two processes (in other words: two methods; in other words: two sub-methods; in other words: two phases), namely step locking (which may include steps 210, 212, 214, 216, 218 of FIG. 2) and step tracking (which may include steps 222, 224, 226, 228 and 230 of FIG. 2). These measurements may be performed on filtered data.

In 208, it may be determined whether a dominant axis is found (in other words: whether a dominant axis has been found; in other words: whether a dominant axis has been locked). In case it is determined in 208 that a dominant axis is not found, processing may continue with step 210. In case it is determined in 208 that a dominant axis is found, processing may continue with step 222.

In the first process (step locking), the dominant axis of the acceleration signal may be located. During this phase, like indicated by box 210, the acceleration data from all the axes may be analyzed. In other words, in 210, for all axis, a step frequency may be computed from the filtered data.

It will be understood that each of the steps 210, 212, 214, 216, 218, and 220 may be carried out for each axis for which acceleration data, is available (for example for all three axes in case of a three-axes-accelerometer).

In 212, it may be determined whether the (step) frequency is within a pre-determined range of frequencies (which may be referred to as the tracking range). In case it is determined in 212 that the (step) frequency is not within the pre-determined range of frequencies, processing may continue in 220. In case it is determined in 212 that the (step) frequency is within the pre-determined range of frequencies, processing may continue in 214.

In 214, it may be determined whether the acceleration is greater than a pre-determined threshold (which may be referred to as minimum threshold). In case it is determined in 214 that the acceleration is not greater than the pre-determined threshold, processing may continue in 220. In case it is determined in 214 that the acceleration is greater than the pre-determined threshold, processing may continue in 216.

In 216, it may be determined whether at least a pre-determined number of cycles is detected (in other words, whether a minimum number of cycles is detected). In case it is determined in 216 that less than the pre-determined number of cycles is detected, processing may continue in 220. In case it is determined in 216 that at least a pre-determined number of cycles is detected, processing may continue in 218.

In 218, the dominant axis may be assigned (for example the axis for which the processing in steps 212, 214, and 216 has been performed may be assigned as the dominant axis).

In 220, processing may restart, for example may continue with the next axis, which may be processed in a round-robin manner, or with a new set of filtered data (for example starting with the first axis again).

According to various embodiments, the purpose may be to detect a periodic signal, which fulfills the following requirements:

(1) Frequency is in a pre-determined range (for example between 0.2 Hz and 20 Hz; or for example between 0.5 Hz and 5 Hz; or for example between 1 Hz and 4 Hz);

(2) The (step) frequency jitter (in other words: the frequency variation) between each cycle is within a predetermined tolerance range (for example in a range between 20% and 80%; for example in a range between 40% and 60%; for example 40%; for example 50%; for example 60%) from (or of) the previous cycle;

(3) The amplitude swing (in other words: the amplitude variation) between each cycle is within a predetermined tolerance range (for example in a range between 20% and 80%; for example in a range between 40% and 60%; for example 40%; for example 50%; for example 60%) from (or of) previous cycle; and (4) The acceleration is greater than a predefined threshold (for walking activity). The threshold (in other words: acceleration threshold) may be set at 0.01 g, or may be set at 0.1 g, or may be set at 0.5 g, wherein g is a unit of acceleration equal to the acceleration of gravity at the earth's surface (for example about 9.81 m/s$^2$).

According to various embodiments, the dominant axis may be locked when the system is able to detect a minimum number of cycles that meet the conditions stated above.

According to various embodiments, the step mode (for example full cycle or half cycle) may be determined by checking the middle point of the acceleration. The middle point (in other words: mid point) may indicate the position of the sensor device at rest. According to various embodiments, half cycle mode may be chosen if the mid point is closed to zero. According to various embodiments, full cycle mode may be chosen otherwise.

According to various embodiments, the second phase may be step tracking (which may be carried out in steps 222, 224, 226, 228, and 230 of FIG. 2). In 222, it may be determined whether the frequency of acceleration data is within the tracking range. In 224, it may be determined whether the acceleration is greater than a minimum threshold. In 226, the step mode may be determined based on raw data. In this phase, a step count may be registered (in other words a step count may be added in 230) when the acceleration data meet the four conditions of the first phase. If step mode is full cycle (which may be determined in 228), one step count may be added to the system when the acceleration data complete a full sine wave cycle, whereas two step counts may be added to the system if the step mode is half cycle. The tracking phase may end when the acceleration data do not meet the four conditions in the first phase. The first phase (locking) may be to count the number of steps taken; the second phase (tracking) may be to track the acceleration data to make sure that it is a continuation from current walking activity.

According to various embodiments, devices, systems and/or methods may be provided with utilize an inertial sensor disposed at one of a plurality of locations on a human body, such as the ankles and feet. The inertial sensor may be configured to measure acceleration along a dominant axis, and also measure linear as well as rotational accelerations. A step count, i.e., number of steps taken, may be determined by measuring and filtering the acceleration data generated by the sensor. The system and method may provide an enhanced step count accuracy even while simultaneous parts of the body, such as the arms, are moving. Also, less CPU processing may be utilized since the middle point of the acceleration data, and filtering is utilized to determine the step count.

According to various embodiments, raw acceleration data may initially be gathered by the sensor from various movements from the body. The movements may include repetitive raising and lowering of the legs in a stepping motion, or swinging of the arms. The raw acceleration data may be filtered through a low pass filter to comb through high frequency, noise, and an averaging filter to remove the DC component. A frequency may be derived from this raw acceleration data.

In a step locking mode, the dominant axis may be separated from other axes to detect a periodic signal (for example to detect a frequency). The step count may be determined when a minimum threshold for the frequency is met (for example, frequency is in a pre-determined range; and frequency jitter from each cycle is within a predetermined range of prior cycle). In a step tracking mode, the middle point of acceleration of the sensor may be detected to calculate the step count. For example, a one-step count may be added to the system when the acceleration data completes a full sine wave cycle, whereas a two-step counts may be added to the system if the step mode is half cycle.

The following examples pertain to further embodiments.

Example 1 is a step counter device comprising: an accelerometer configured to determine an acceleration in each axis of a plurality of axes; a dominant axis determination circuit configured to determine one axis of the plurality of axis as a dominant axis based on determining, for each axis of the plurality of axis, a plurality of criteria for the respective axis; a step number determination circuit configured to determine a number of steps based on determining the plurality of criteria for the dominant axis; wherein the criteria for a respective axis comprise a criterion indicating whether a frequency of acceleration in the respective axis is within a first pre-determined range, a criterion indicating whether a variation in the frequency of acceleration in the respective axis between various cycles is within a second pre-determined range; a criterion indicating whether a variation in the amplitude of acceleration in the respective axis between various cycles is within a third pre-determined range; and a criterion indicating whether the acceleration in the respective axis is higher than a pre-determined threshold.

In example 2, the subject-matter of example 1 can optionally include a frequency determination circuit configured to determine for a respective axis of the plurality of axis the criterion indicating whether the frequency of acceleration in the respective axis is within a pre-determined range.

In example 3, the subject-matter of any one of examples 1 to 2 can optionally include a frequency variation determination circuit configured to determine for a respective axis of the plurality of axis the criterion indicating whether the variation in the frequency of acceleration in the respective axis between various cycles is within a pre-determined range.

In example 4, the subject-matter of any one of examples 1 to 3 can optionally include an amplitude variation determination circuit configured to determine for a respective axis of the plurality of axis the criterion indicating whether the variation in the amplitude of acceleration in the respective axis between various cycles is within a pre-determined range.

In example 5, the subject-matter of any one of examples 1 to 4 can optionally include an amplitude determination circuit configured to determine for a respective axis of the plurality of axis the criterion indicating whether the acceleration in the respective axis is higher than a pre-determined threshold.

In example 6, the subject-matter of any one of examples 1 to 5 can optionally include that the first pre-determined range comprises at least one of: a range of 0.2 Hz to 20 Hz; a range of 0.5 Hz to 5 Hz; and a range of 1 Hz to 4 Hz.

In example 7, the subject-matter of any one of examples 1 to 6 can optionally include that the second pre-determined range comprises at least one of: a range of 20% to 80%; a range of 40% to 60%; a value of at least substantially 40%; a value of at least substantially 50%; and a value of at least substantially 60%.

In example 8, the subject-matter of any one of examples 1 to 7 can optionally include that the third pre-determined range comprises at least one of: a range of 20% to 80%; a range of 40% to 60%; a value of at least substantially 40%; a value of at least substantially 50%; and a value of at least substantially 60%.

In example 9, the subject-matter of any one of examples 1 to 8 can optionally include that the pre-determined threshold is one of 0.01 g, or 0.1 g, or 0.5 g.

In example 10, the subject-matter of any one of examples 1 to 9 can optionally include that the dominant axis determination circuit is further configured to determine the dominant axis based on determining, for each axis of the plurality of axes, a criterion indicating whether the acceleration in the respective axis includes at least a pre-determined number of cycles.

In example 11, the subject-matter of any one of examples 1 to 10 can optionally include a cycle determination circuit configured to determine a cycle of acceleration in any one of the plurality of axes.

In example 12, the subject-matter of any one of examples 1 to 11 can optionally include a step mode determination circuit configured to determine a step mode based on the accelerations determined by the accelerometer.

In example 13, the subject-matter of any one of examples 1 to 12 can optionally include a middle point determination circuit configured to determine a middle point in the accelerations determined by the accelerometer.

In example 14, the subject-matter of example 13 can optionally include a step mode determination circuit configured to determine a step mode based on the determined middle point.

In example 15, the subject-matter of any one of examples 1 to 14 can optionally include that the step counter device is provided in a wearable device.

Example 16 is a step counting method comprising: determining an acceleration in each axis of a plurality of axes; determining one axis of the plurality of axis as a dominant axis based on determining, for each axis of the plurality of axis, a plurality of criteria for the respective axis; determining a number of steps based on determining the plurality of criteria for the dominant axis; wherein the criteria for a respective axis comprise a criterion indicating whether a frequency of acceleration in the respective axis is within a first pre-determined range, a criterion indicating whether a variation in the frequency of acceleration in the respective axis between various cycles is within a second pre-determined range; a criterion indicating whether a variation in the amplitude of acceleration in the respective axis between various cycles is within a third pre-determined range; and a criterion indicating whether the acceleration in the respective axis is higher than a pre-determined threshold.

In example 17, the subject-matter of example 16 can optionally include determining for a respective axis of the plurality of axis the criterion indicating whether the frequency of acceleration in the respective axis is within a pre-determined range.

In example 18, the subject-matter of any one of examples 16 to 17 can optionally include determining for a respective axis of the plurality of axis the criterion indicating whether the variation in the frequency of acceleration in the respective axis between various cycles is within a pre-determined range.

In example 19, the subject-matter of any one of examples 16 to 18 can optionally include determining for a respective axis of the plurality of axis the criterion indicating whether the variation in the amplitude of acceleration in the respective axis between various cycles is within a pre-determined range.

In example 20, the subject-matter of any one of examples 16 to 19 can optionally include determining for a respective axis of the plurality of axis the criterion indicating whether the acceleration in the respective axis is higher than a pre-determined threshold.

In example 21, the subject-matter of any one of examples 16 to 20 can optionally include that the first pre-determined range comprises at least one of: a range of 0.2 Hz to 20 Hz; a range of 0.5 Hz to 5 Hz; and a range of 1 Hz to 4 Hz.

In example 22, the subject-matter of any one of examples 16 to 21 can optionally include that the second pre-determined range comprises at least one of: a range of 20% to 80%; a range of 40% to 60%; a value of at least substantially 40%; a value of at least substantially 50%; and a value of at least substantially 60%.

In example 23, the subject-matter of any one of examples 16 to 22 can optionally include that the third pre-determined range comprises at least one of: a range of 20% to 80%; a range of 40% to 60%; a value of at least substantially 40%; a value of at least substantially 50%; and a value of at least substantially 60%.

In example 24, the subject-matter of any one of examples 16 to 23 can optionally include that the pre-determined threshold is one of 0.01 g, or 0.1 g, or 0.5 g.

In example 25, the subject-matter of any one of examples 16 to 24 can optionally include determining the dominant axis based on determining, for each axis of the plurality of axes, a criterion indicating whether the acceleration in the respective axis includes at least a pre-determined number of cycles.

In example 26, the subject-matter of any one of examples 16 to 25 can optionally include determining a cycle of acceleration in any one of the plurality of axes.

In example 27, the subject-matter of any one of examples 16 to 26 can optionally include determining a step mode based on the determined accelerations.

In example 28, the subject-matter of any one of examples 16 to 27 can optionally include determining a middle point in the determined accelerations.

In example 29, the subject-matter of example 28 can optionally include determining a step mode based on the determined middle point.

In example 30, the subject-matter of any one of examples 16 to 29 can optionally include that the step counting method is performed in a wearable device.

While the invention has been particularly shown and described with reference to specific embodiments, it should be understood by those skilled in the art that various changes in form and detail may be made therein without departing from the spirit and scope of the invention as defined by the appended claims. The scope of the invention is thus indicated by the appended claims and all changes which come within the meaning and range of equivalency of the claims are therefore intended to be embraced.

The invention claimed is:

1. A step counter device comprising:
an accelerometer configured to determine an acceleration in each axis of a plurality of axes;
a dominant axis determination circuit configured to determine one axis of the plurality of axes to be a dominant axis based on determining, for each axis of the plurality of axes, a first plurality of criteria for the respective axis comprising a criterion indicating whether a frequency of a periodic signal of the acceleration in the respective axis is within a first pre-determined range, a criterion indicating whether a frequency jitter of the periodic signal of the acceleration in the respective axis between cycles within the periodic signal is within a second pre-determined range, a criterion indicating whether a variation in an amplitude of the acceleration in the respective axis between the cycles is within a third pre-determined range, a criterion indicating whether the acceleration in the respective axis is higher than a pre-determined threshold, and a criterion indicating whether periodic signal of the acceleration in the respective axis includes at least a pre-determined number of cycles;

wherein the axis that fulfils the first plurality of criteria is determined by the dominant axis determination circuit to be the dominant axis;
a step number determination circuit configured to determine a number of steps based on determining whether the determined dominant axis fulfils a second plurality of criteria comprising
a criterion indicating whether a frequency of a periodic signal of the acceleration in the respective axis is within a first pre-determined range, a criterion indicating whether a frequency jitter of the periodic signal of the acceleration in the respective axis between cycles within the periodic signal is within a second pre-determined range, a criterion indicating whether a variation in an amplitude of the acceleration in the respective axis between the cycles is within a third pre-determined range, and a criterion indicating whether the acceleration in the respective axis is higher than a pre-determined threshold;
wherein a step count is registered when the determined dominant axis fulfils the second plurality of criteria.

2. The step counter device of claim 1, further comprising at least one of:
a frequency determination circuit configured to determine for the respective axis the criterion indicating whether the frequency of the periodic signal of the acceleration in the respective axis is within the first pre-determined range,
a frequency variation determination circuit configured to determine for the respective axis the criterion indicating whether the frequency jitter of the periodic signal of the acceleration in the respective axis between the cycles within the periodic signal is within the second pre-determined range, an amplitude variation determination circuit configured to determine for the respective axis the criterion indicating whether the variation in the amplitude of the acceleration in the respective axis between the cycles is within the third pre-determined range, or
an amplitude determination circuit configured to determine for the respective axis the criterion indicating whether the acceleration in the respective axis is higher than the pre-determined threshold.

3. The step counter device of claim 1,
wherein the first pre-determined range comprises at least one of: a range of 0.2 Hz to 20 Hz; a range of 0.5 Hz to 5 Hz; and a range of 1 Hz to 4 Hz.

4. The step counter device of claim 1,
wherein the second pre-determined range comprises at least one of: a range of 20% to 80%; a range of 40% to 60%; a value of at least 40%; a value of at least 50%; and a value of at least 60%.

5. The step counter device of claim 1,
wherein the third pre-determined range comprises at least one of: a range of 20% to 80%; a range of 40% to 60%; a value of at least 40%; a value of at least 50%; and a value of at least 60%.

6. The step counter device of claim 1,
wherein the pre-determined threshold is one of 0.01 g, or 0.1 g, or 0.5 g.

7. The step counter device of claim 1, further comprising at least one of:
a cycle determination circuit configured to determine a cycle of acceleration in any one of the plurality of axes, or a step mode determination circuit configured to determine a step mode based on the accelerations determined by the accelerometer.

8. The step counter device of claim 1, further comprising:
a middle point determination circuit configured to determine a middle point in the accelerations determined by the accelerometer.

9. The step counter device of claim 8, further comprising:
a step mode determination circuit configured to determine a step mode based on the determined middle point;
wherein a first step mode is determined when the middle point has a first value; and
wherein a second step mode is determined when the middle point has a second value.

10. The step counter device of claim 1,
wherein the step counter device is provided in a wearable device.

11. A step counting method comprising:
determining an acceleration in each axis of a plurality of axes;
determining one axis of the plurality of axes to be a dominant axis based on determining, for each axis of the plurality of axes, a first plurality of criteria for the respective axis comprising a criterion indicating whether a frequency of a periodic signal of the acceleration in the respective axis is within a first pre-determined range, a criterion indicating whether a frequency jitter of the periodic signal of the acceleration in the respective axis between cycles within the periodic signal is within a second pre-determined range, a criterion indicating whether a variation in an amplitude of the acceleration in the respective axis between the cycles is within a third pre-determined range, a criterion indicating whether the acceleration in the respective axis is higher than a pre-determined threshold, and a criterion indicating whether periodic signal of the acceleration in the respective axis includes at least a pre-determined number of cycles;
wherein the axis that fulfils the first plurality of criteria is determined to be the dominant axis;
determining a number of steps based on determining whether the determined dominant axis fulfils a second plurality of criteria comprising
a criterion indicating whether a frequency of a periodic signal of the acceleration in the respective axis is within a first pre-determined range, a criterion indicating whether a frequency jitter of the periodic signal of the acceleration in the respective axis between cycles within the periodic signal is within a second pre-determined range, a criterion indicating whether a variation in an amplitude of the acceleration in the respective axis between the cycles is within a third pre-determined range, and a criterion indicating whether the acceleration in the respective axis is higher than a pre-determined threshold;
wherein a step count is registered when the determined dominant axis fulfils the second plurality of criteria.

12. The step counting method of claim 11,
wherein the first pre-determined range comprises at least one of: a range of 0.2 Hz to 20 Hz; a range of 0.5 Hz to 5 Hz; and a range of 1 Hz to 4 Hz.

13. The step counting method of claim 11,
wherein the second pre-determined range comprises at least one of: a range of 20% to 80%; a range of 40% to 60%; a value of at least 40%; a value of at least 50%; and a value of at least 60%.

14. The step counting method of claim 11,
wherein the third pre-determined range comprises at least one of: a range of 20% to 80%; a range of 40% to 60%; a value of at least 40%; a value of at least 50%; and a value of at least 60%.

15. The step counting method of claim 11,
wherein the pre-determined threshold is one of 0.01 g, or 0.1 g, or 0.5 g.

16. The step counting method of claim 11, further comprising at least one of:
   determining a cycle of acceleration in any one of the plurality of axes, or
   determining a step mode based on the determined accelerations.

17. The step counting method of claim 11, further comprising:
   determining a middle point in the determined accelerations.

18. The step counting method of claim 17, further comprising:
   determining a step mode based on the determined middle point;
   wherein a first step mode is determined when the middle point has a first value; and
   wherein a second step mode is determined when the middle point has a second value.

* * * * *